(12) United States Patent
Andreassen et al.

(10) Patent No.: US 10,966,600 B2
(45) Date of Patent: Apr. 6, 2021

(54) DIGITAL OTOSCOPE

(71) Applicant: Welch Allyn, Inc., Skaneateles Falls, NY (US)

(72) Inventors: Eric M. Andreassen, Syracuse, NY (US); David M. Fallat, Auburn, NY (US); Ervin Goldfain, Syracuse, NY (US); John R. Strom, Moravia, NY (US); John T. Delaney, Auburn, NY (US); Howard Haines, Auburn, NY (US); Corinn C. Fahrenkrug, Liverpool, NY (US); Cynthia A. Kuiper, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 16/904,676

(22) Filed: Jun. 18, 2020

(65) Prior Publication Data
US 2020/0315442 A1   Oct. 8, 2020

Related U.S. Application Data

(60) Continuation of application No. 16/677,950, filed on Nov. 8, 2019, which is a continuation of application
(Continued)

(51) Int. Cl.
*A61B 1/227* (2006.01)
*A61B 1/00* (2006.01)

(52) U.S. Cl.
CPC .......... *A61B 1/227* (2013.01); *A61B 1/00096* (2013.01)

(58) Field of Classification Search
CPC ....... A61B 1/227; A61B 1/00096; A61B 1/04; A61B 1/05; A61B 1/06; A61B 1/0661
See application file for complete search history.

(56) References Cited

U.S. PATENT DOCUMENTS 3,698,387 A   10/1972  Moore et al.
3,840,004 A   10/1974  Heine
(Continued)

FOREIGN PATENT DOCUMENTS

SU            501374       10/1976
WO         WO99/42760       8/1999
(Continued)

OTHER PUBLICATIONS

International Search Report and Written Opinion of the International Searching Authority for International Application No. PCT/US07/653367, dated Jun. 3, 2008 (10 pages).
(Continued)

*Primary Examiner* — Lynnsy M Summitt
*Assistant Examiner* — Christina NegrelliRodriguez
(74) *Attorney, Agent, or Firm* — Barclay Damon LLP (57) ABSTRACT

An otoscope includes an instrument head, a tip element and an optical system. The instrument head has a distal insertion portion for insertion into an ear of a human or veterinary subject. The distal insertion portion has a distal opening. The tip element is releasably attached to the distal insertion portion. The tip element has a distal opening. The optical system is contained within the instrument head. The optical system includes a plurality of optical components. The optical system further comprises a viewing component for viewing of an image of a target of interest aligned along an optical axis disposed within said distal opening. The optical system is configured to provide a field of having a diameter equaling at least 7 mm at a distance of at least 15 mm from a distal opening of said attached tip element. The optical system is further configured to simultaneously provide a distance range of optimal focus having a range of at least 8 mm. The distance range of optimal focus includes a location at a working distance equal to about 30 mm.

17 Claims, 6 Drawing Sheets

Related U.S. Application Data

No. 15/332,110, filed on Oct. 24, 2016, now Pat. No. 10,470,650, which is a continuation of application No. 13/899,803, filed on May 22, 2013, now Pat. No. 9,474,441, which is a division of application No. 13/237,022, filed on Sep. 20, 2011, now Pat. No. 8,469,882, which is a division of application No. 11/845,512, filed on Aug. 27, 2007, now Pat. No. 8,066,634, which is a continuation-in-part of application No. 10/897,590, filed on Jul. 23, 2004, now Pat. No. 7,399,275.

(60) Provisional application No. 60/543,858, filed on Feb. 11, 2004, provisional application No. 60/507,473, filed on Sep. 30, 2003, provisional application No. 60/490,566, filed on Jul. 28, 2003.

(56) References Cited

U.S. PATENT DOCUMENTS

| | | |
|---|---|---|
| 4,366,811 A | 1/1983 | Riester |
| 4,659,187 A | 4/1987 | Tsuji et al. ............... 359/688 |
| 4,662,360 A | 5/1987 | O'Hara et al. |
| 4,785,796 A | 11/1988 | Mattson |
| 4,997,419 A | 3/1991 | Lakatos et al. |
| 5,093,719 A | 3/1992 | Prescott ............... 348/65 |
| 5,363,839 A | 11/1994 | Lankford |
| 5,390,663 A | 2/1995 | Schaefer |
| 5,624,453 A | 4/1997 | Ahmed |
| 5,658,235 A | 8/1997 | Priest et al. ............... 600/112 |
| 5,720,756 A | 2/1998 | Green et al. |
| 5,795,067 A | 8/1998 | Fraden et al. |
| 5,842,971 A | 12/1998 | Yoon |
| 5,919,130 A | 7/1999 | Monroe et al. ............... 600/200 |
| 6,010,450 A | 1/2000 | Perkins ............... 600/175 |
| 6,019,721 A | 2/2000 | Holmes et al. |
| 6,053,875 A | 4/2000 | Rosenbaum et al. |
| 6,099,537 A | 8/2000 | Sugai et al. |
| 6,106,457 A | 8/2000 | Perkins ............... A61B 1/00041 396/312 |
| 6,129,661 A | 10/2000 | Iafrati et al. |
| 6,142,934 A | 11/2000 | Lagerway ............... A61B 1/00041 500/200 |
| 6,190,310 B1 | 2/2001 | Cook |
| 6,213,938 B1 | 4/2001 | Cook |
| 6,254,271 B1 | 7/2001 | Lin |
| 6,383,133 B1 | 5/2002 | Jones |
| 6,398,724 B1 | 6/2002 | May et al. ............... 600/167 |
| 6,425,857 B1 | 7/2002 | Rudischhauser et al. |
| 6,450,970 B1 | 9/2002 | Mahler ............... A61B 1/227 600/549 |
| 6,475,138 B1 | 11/2002 | Schechter et al. |
| 6,511,420 B1 | 1/2003 | Farrell et al. |
| 6,537,208 B1 | 3/2003 | Konno ............... 600/167 |
| 6,554,765 B1 | 4/2003 | Yarush et al. |
| 7,029,439 B2 | 4/2006 | Roberts et al. |
| 7,177,088 B2 | 2/2007 | Hirata ............... 359/659 |
| 7,399,275 B2 | 7/2008 | Goldfain et al. |
| 7,471,458 B2 | 12/2008 | Straehle et al. ............... 359/656 |
| 7,803,110 B2 | 9/2010 | Goldfain et al. |
| 2001/0014112 A1 | 8/2001 | Yamaka |
| 2002/0038075 A1* | 3/2002 | Tsai ............... A61B 1/00052 600/200 |
| 2002/0085616 A1 | 7/2002 | Yu |
| 2002/0193665 A1 | 12/2002 | Jones |
| 2003/0050533 A1 | 3/2003 | Minami ............... 600/168 |
| 2003/0063386 A1 | 4/2003 | Slawson et al. |
| 2003/0139671 A1* | 7/2003 | Walston ............... A61B 8/4427 600/437 |
| 2004/0186352 A1 | 9/2004 | Roberts ............... G02B 6/0006 600/200 |
| 2005/0027168 A1 | 2/2005 | Strom et al. |
| 2005/0027169 A1 | 2/2005 | Goldfain et al. |
| 2005/0043588 A1 | 2/2005 | Tsai |
| 2006/0020176 A1 | 1/2006 | Berall |
| 2006/0159155 A1 | 7/2006 | Lantz et al. |
| 2007/0010711 A1 | 1/2007 | Hasegawa ............... 600/168 |
| 2008/0051637 A1 | 2/2008 | Andreassen et al. |

FOREIGN PATENT DOCUMENTS

| | | |
|---|---|---|
| WO | WO 99/42760 | 8/1999 |
| WO | WO 02/056756 A2 | 7/2002 |
| WO | WO 2002/055756 A2 | 7/2002 |

OTHER PUBLICATIONS

European Search Report for EP Application No. 08798437.3; dated Oct. 27, 2010, 7 pages.

International Search Report, dated Mar. 10, 2009, PCT/US2008/073956 (4 pgs.).

Australian Office Action for AU Application No. 2008293684, dated Nov. 7, 2012, 4 pages.

* cited by examiner

DIGITAL OTOSCOPE

CROSS REFERENCE TO RELATED APPLICATIONS

This patent application is a continuation application of, and claims priority and benefit to, co-pending U.S. patent application Ser. No. 16/677,950, filed Nov. 8, 2019, entitled "Digital Otoscope", which is a continuation of U.S. patent application Ser. No. 15/332,110, filed Oct. 24, 2016, entitled "Digital Otoscope" and now issued U.S. Pat. No. 10,470,650, which is a continuation of U.S. patent application Ser. No. 13/899,803, filed May 22, 2013, entitled "Digital Otoscope" and now issued U.S. Pat. No. 9,474,441, which is a divisional application of U.S. patent application Ser. No. 13/237,022, filed Sep. 20, 2011, entitled "Digital Otoscope" and now issued U.S. Pat. No. 8,469,882, which is a divisional application of U.S. patent application Ser. No. 11/845,512, filed Aug. 27, 2007, entitled "Digital Otoscope" and now issued U.S. Pat. No. 8,066,634, which is a continuation-in-part application of U.S. patent application Ser. No. 10/897,590, filed Jul. 23, 2004, entitled "Otoscope" and now issued U.S. Pat. No. 7,399,275, which claims priority based upon the following provisional patent applications: U.S. Patent Application Ser. No. 60/490,566, filed Jul. 28, 2003; U.S. Patent Application Ser. No. 60/507,473, filed Sep. 30, 2003; and U.S. Patent Application Ser. No. 60/543,858, filed Feb. 11, 2004. All of the aforementioned patent(s) and patent application(s) are herein incorporated by reference in their entirety.

FIELD OF THE INVENTION

This invention relates generally to an otoscope that incorporates an image forming device, such as a digital camera, and in particular to an otoscope further providing optical characteristics that enhance medical inspection of both human and veterinary subjects.

BACKGROUND OF THE INVENTION

An otoscope is used for inspection of an ear canal or a nasal cavity. Typically, a prior art otoscope includes one or more lenses providing a fixed magnification of light received, without providing a separate mechanism for adjusting focus over any significant range, if over any range at all. Whether a particular target within the ear canal, such as the tympanic membrane (ear drum), is at or near optimal focus with respect to the observing eye of a medical practitioner, generally depends upon the location of the otoscope with respect to the target.

SUMMARY OF THE INVENTION

In one aspect, the invention provides for a digital otoscope for forming (imaging) live and still digital images of anatomical details of a body of a human or veterinary subject, and having associated optical characteristics that improve the quality of visual information gathered for medical inspection of both human and veterinary subjects.

The digital otoscope is configured to attach to a tip element having dimensions that are small enough to fit into a small body cavity, such as an ear canal, nasal cavity or throat cavity, for example. An attached tip element can be selected from a plurality of different tip elements that are each configured to attach to the otoscope 1000. An attached tip element and the otoscope 1000 enclose an assembly of optical components yielding optical characteristics that provide a substantially wide field of view and a substantially wide range of optimal focus from which to form visual information within a small and confined ear, nasal or throat cavity, for example.

In some embodiments, the tip element is configured to be inserted at least 15 mm into a representative human ear canal, and configured to provide optical characteristics that include a field of view of at least 7 mm at a distance of less than 10 mm from a distal end of the tip element, and a distance range of optimal focus starting at less than 5 mm from a distal end of the tip element and extending greater than 20 mm from a distal end of the tip element.

The foregoing as well as other objects, aspects, features, and advantages of the invention will become more apparent from the following description and from the claims.

BRIEF DESCRIPTION OF THE DRAWINGS

The objects and features of the invention can be better understood with reference to the claims and drawings described below. The drawings are not necessarily to scale, the emphasis is instead generally being placed upon illustrating the principles of the invention. Within the drawings, like reference numbers are used to indicate like parts throughout the various views. Differences between like parts may cause those parts to be indicated by different reference numbers. Unlike parts are indicated by different reference numbers.

DETAILED DESCRIPTION OF THE INVENTION

Figure 1:
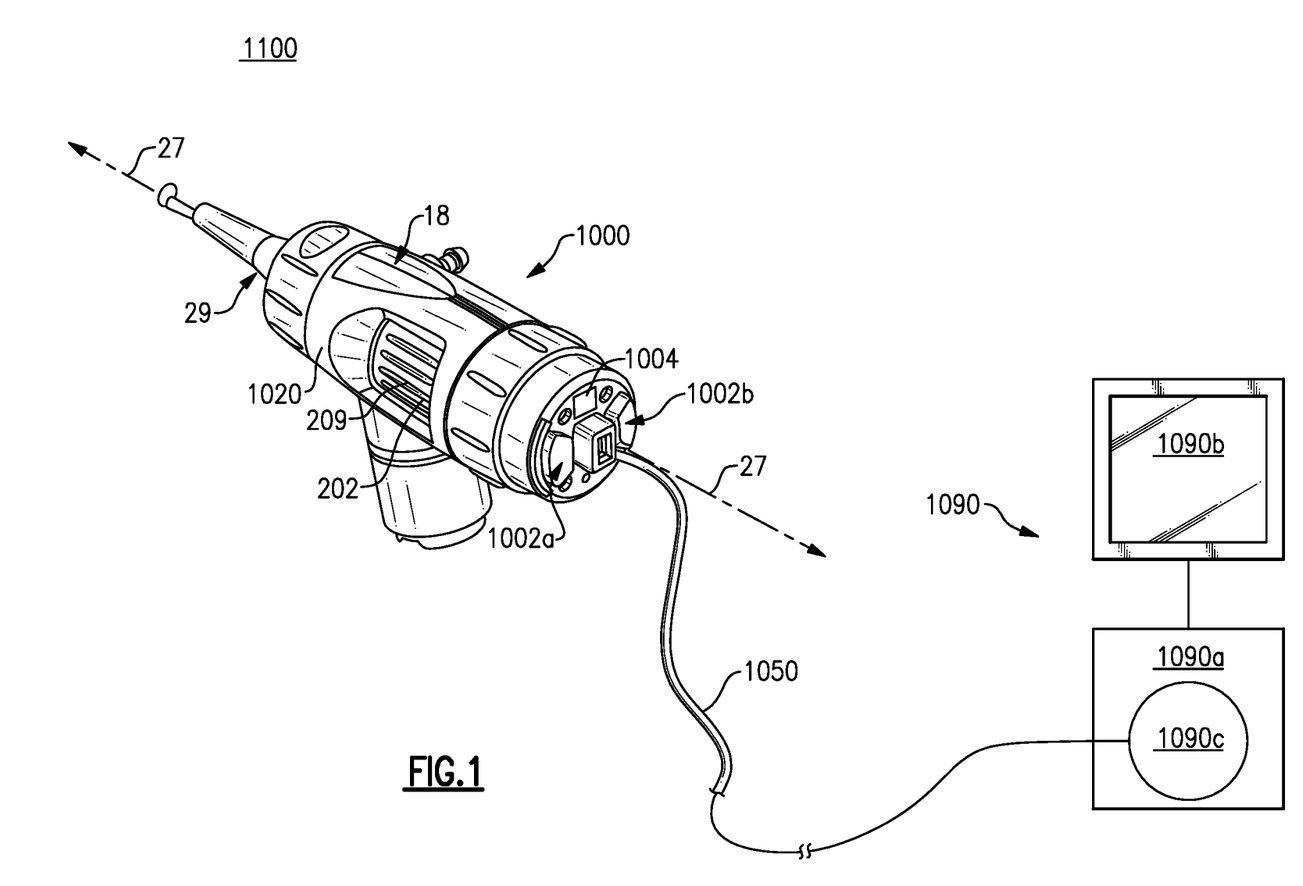
FIG. 1 illustrates a top perspective view of an embodiment of a digital otoscope that incorporates a digital image forming device and that is in communication with a computing device via a communications channel.

FIG. 1 illustrates a top perspective view of an embodiment of a digital otoscope 1000 that incorporates a digital image forming device (See FIGS. 2-3) and that is in communication with a computing device 1090 via a first communications channel 1050. In this embodiment, the image forming device is implemented as a digital camera and the communications channel 1050 is implemented as a wireline (cable connection) type of communications channel 1050 and the computing device 1090 is implemented as a personal computer 1090.

Figure 2:
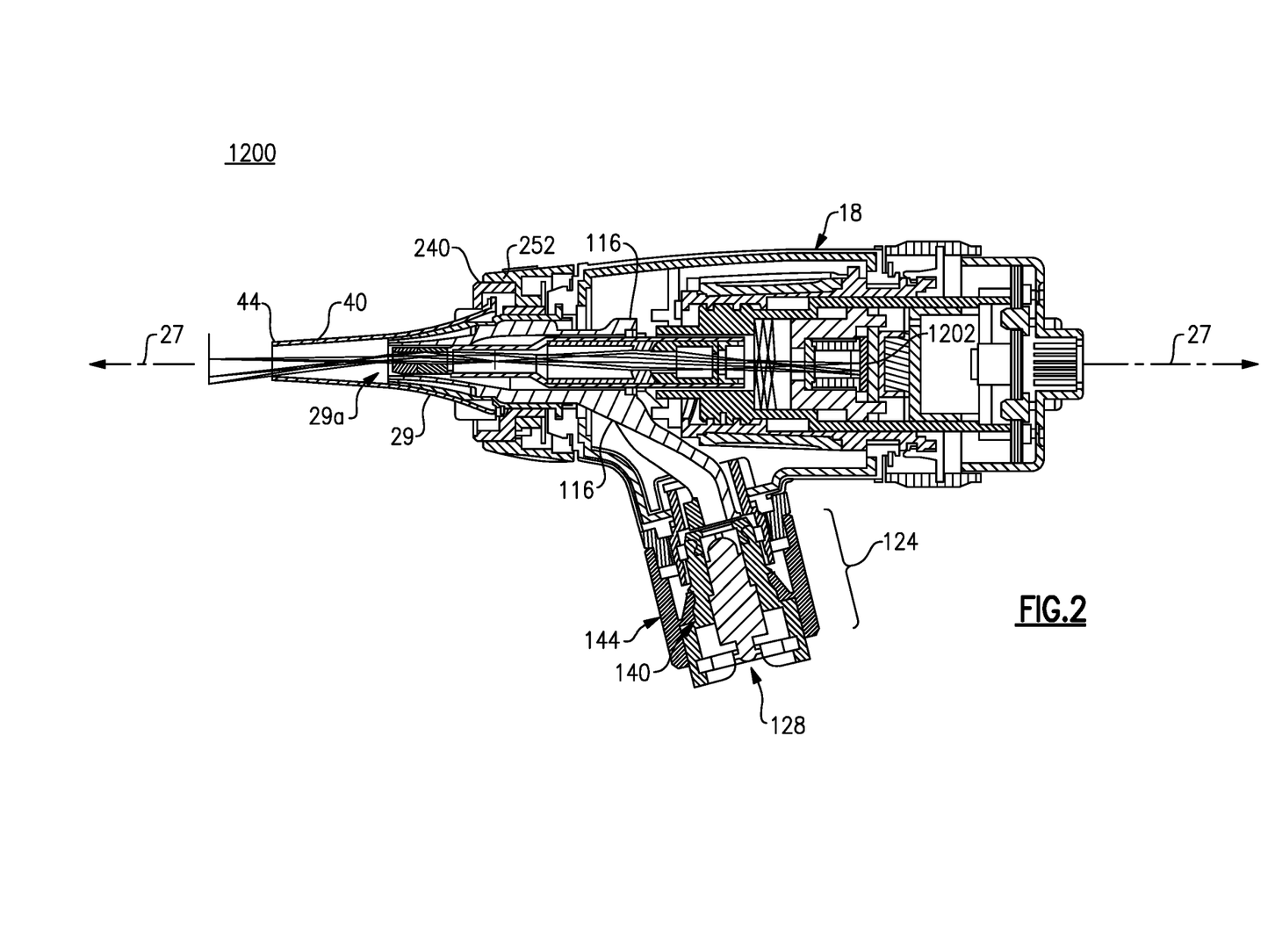
FIG. 2 illustrates a side cross-sectional view of the embodiment of the digital otoscope.
Figure 3:
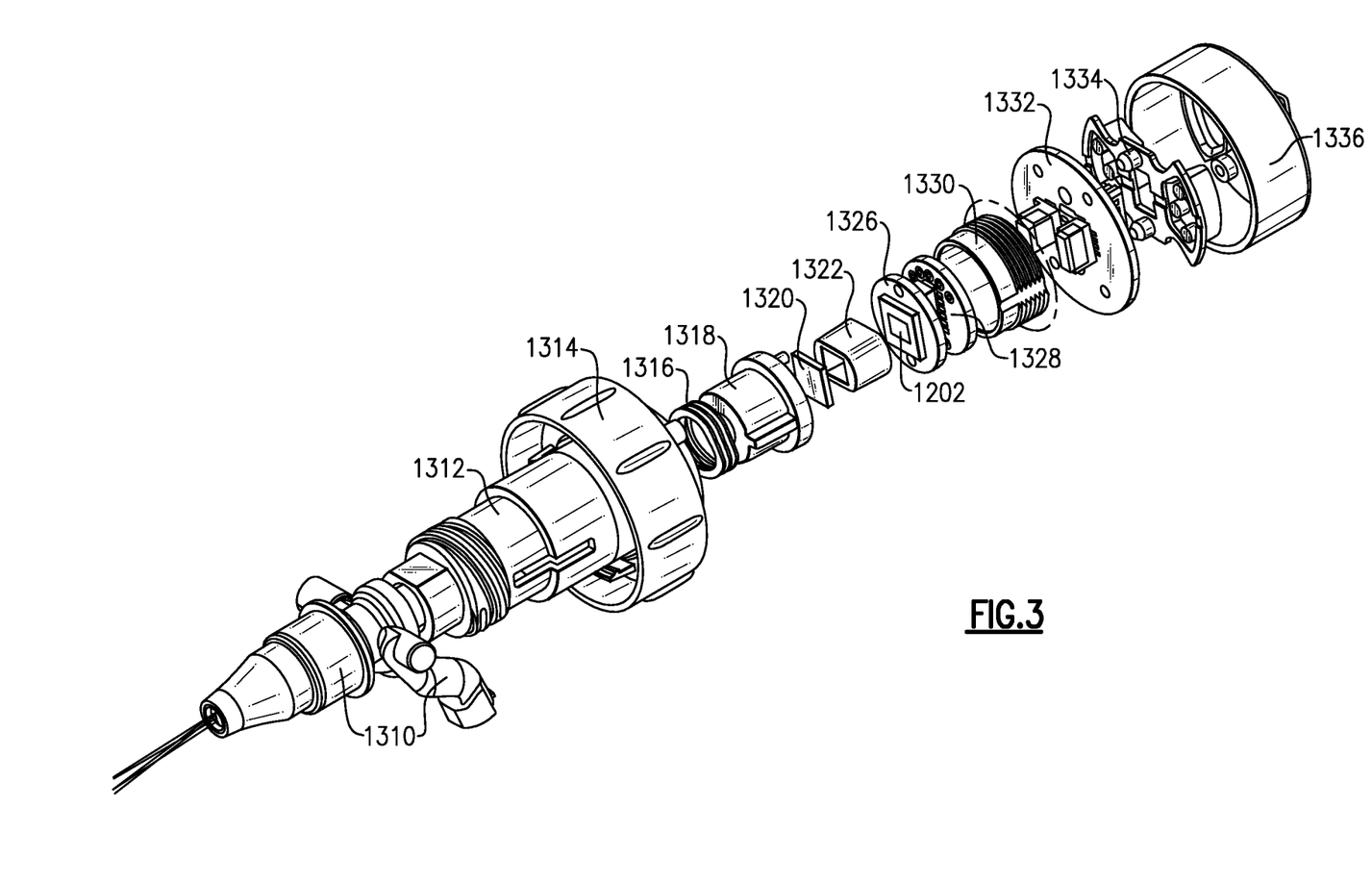
FIG. 3 illustrates an exploded view of internal components of the embodiment of the digital otoscope.

In this embodiment, the digital camera is embedded into the housing of the digital otoscope 1000 (See FIGS. 2-3). The digital camera is configured to form image information that represents a still or a live image. In this embodiment, the digital camera is implemented as a Micron ⅓ Inch SOC Megapixel CMOS Digital Image Sensor, also referred to herein as the image sensor or imager. In other embodiments, other models of digital cameras from the same or different suppliers, are employed to function as the image forming device.

As shown, the otoscope 1000 includes an instrument head 18 including a surrounding housing 1020 and a distal insertion portion 29 that is insertable into an ear canal. An optical axis 27 is defined as being nearly (proximately) centric to a field of view of the imager. A focus position visual indicator 209 is located along a surface 202, also referred to as a recessed surface 202, that is recessed with respect to the surface of the housing 1020. The recessed surface 202 is a grippable elastomeric cover 202 that is configured so that a user of the otoscope 1000 can press against and push it in a direction that is tangential to its surface 202, to rotate it around the optical axis 27.

The imager forms live (moving) or still images using an array of 1280×1024 pixels having an aspect ratio of (5:4). While operating in a live mode, the imager streams (communicates over time) live images while employing an interspersed 640×512 subset (one quarter)) of the array of pixels, herein referred to as currently active pixels. The remaining interspersed pixels are blanked and herein referred to as currently inactive pixels. While operating in live mode, upon capturing a still image, the imager instead employs all 1280×1024 pixels to represent the formed still image, utilizing all pixels as currently active pixels.

In this embodiment, live images are streamed (communicated) in real time without any significant portion of the live image being first stored within the otoscope 1000. In other embodiments, at least a significant portion of a live image is stored within the otoscope 1000 before and if any communication of the live image is performed.

Typically, the formed image information represents a view of tissue within a portion of a body cavity such as an ear canal or nasal cavity. While being formed, the object of interest is located within a field of view of the otoscope 1000 (See FIG. 5). The diameter (linear extent) of the field of view is determined by optical characteristics of the otoscope 1000. The field of view can be altered via a zoom magnification mode. When the zoom magnification mode is on, a center portion (subset) of the default field of view is magnified and represented by the currently active pixels. The default field of view is active when the zoom magnification mode is off.

While operating with zoom magnification mode off, an entire field of view is represented by the currently active pixels. While operating with zoom magnification mode on, a central portion (approximately one-half of the diameter) of the entire field of view is represented by the currently active pixels.

A proximal end of the otoscope 1000 includes to two elastomeric push buttons 1002a-1002b, also referred to as elastomeric switches 1002a-1002b. Two buttons 1002a-1002b are provided to accommodate both right and left handed users of the otoscope 1000. A pressing of either push button (switch) 1002a-1002b causes the imager to form an image, or to toggle a zoom magnification mode of the imager, or to rotate the image currently being formed by 180 degrees.

When either elastomeric push button 1002a-1002b is pressed and released within a span of time that is less than two seconds, the imager forms an image. When either elastomeric button 1002a-1002b is pressed and released in a span of time that is greater than 2 seconds, the imager toggles its zoom magnification mode (off is the (default)). When both elestomeric buttons 1002a-1002b are pressed and released in a span of time that is greater than 4 seconds, the imager rotates an image currently being formed by 180 degrees.

While in use, the otoscope 1000 is designed to be held (oriented) in an upright position (as shown), referred to as a hammer position, or held in an upside down position (not shown), referred to as a pencil position. In other embodiments, the otoscope 1000 includes an accelerometer (not shown) which detects the orientation of the otoscope 1000 in order to reverse the image rotation by 180 degrees, when the otoscope orientation is reversed by 180 degrees.

In this embodiment, the communications channel 1050 is implemented as a universal serial bus (USB) version 2.0. A USB cable connector 1004 is disposed at the rear end of the otoscope 1000. A USB cable 1050, constituting the first communications channel 1050, is attached to a proximal (rear) end of the digital otoscope 1000 via the USB cable connector 1004. The image information formed by the image forming device, namely the imager, is communicated via the communications channel 1050 from the imager to the personal computer 1090, also referred to as a computer 1090. In other embodiments, the image information is stored into memory within the otoscope 1000 before being communicated via the communications channel 1050.

In other embodiments, the otoscope 1000 is configured to provide memory to store digital information, such as including image information. The memory is implemented as volatile random access memory (RAM) or non-volatile flash memory. In some embodiments, the memory is configured to be separable and portable from the otoscope 1000. In some embodiments, the portable memory is implemented a portable universal serial bus (USB 2.0) compatible memory, such as a portable memory that is configured to interoperate with digital cameras, or as portable memory within a thumb drive, provided by suppliers including the Scandisk Corporation.

The computer 1090 is located a distance away from the otoscope 1000. Typically, the distance away at which the computer 1090 is located is within the vicinity of the otoscope 1000, such as within the same room or same office space that the otoscope 1000 is being used. In other embodiments, the computer is located farther from the otoscope 1000.

The first communications channel 1050 enables the digital otoscope 1000 to communicate the image information formed by the imager to the computer 1090 for visual display, and/or for processing, and/or for storage and/or for further communication to another computing device (not shown) via a second communications channel (not shown).

The computer 1090 can be implemented from one of a variety of computing platforms. Preferably, each computing platform executes operating system software 1090c including one or more device drivers for interfacing with devices associated with the computer 1090.

In this embodiment, the computer 1090 executes the Microsoft Windows XP operating system software 1090c and the otoscope 1000 is configured to interoperate with the Windows XP device drivers as a Windows Operating System standard video device. Interoperation is bi-directional so that at least command and configuration information can be communicated from the computer 1090 to otoscope 1000 and image information can be communicated from the otoscope 1000 to the computer 1090.

This embodiment enables the otoscope 1000 to interoperate with the Windows XP operating system software as a plug and play device and further enables a user to utilize a variety of software, including the Windows XP Explorer browser program and other Microsoft Windows based video processing application software, to display and process image information.

Optionally, other operating systems and other browser programs and can be installed and executed by the computer 1090. Preferably, the operating system is compatible with the USB 2.0 standard. For example, the Vista operating system supplied by Microsoft, the Linux operating system, versions of which are supplied from Red Hat and other suppliers, and the Apple Macintosh operating system can be installed and executed on the computer 1090. Other browsers, for example, that are compatible with particular operating systems, such as the Mozilla Firefox or the Apple Safari browsers and can be installed and executed on the computer 1090 where compatible.

The otoscope 1000 includes permanently stored digital logic, also referred to as firmware (not shown), executed by a processor (not shown) that is embedded within the otoscope 1000. The firmware is configured to enable streaming video from the otoscope 1000 to the computer 1090 and downloading of software from the computer 1090 to the otoscope 1000 via the communications channel 1050.

Software that is downloaded to the otoscope 1000 can alter or add to the functionality of the otoscope 1000. For example, downloaded software can recalibrate and/or reprogram the operation of the otoscope 1000. Software, referred to as (otoscope resident) computer interface software, can function to interoperate with the host computer and (host resident) computer interface software, to enhance the interoperation between the otoscope 1000 and the host computer 1090.

In some embodiments, a host device driver and/or other software, referred to as (host resident) computer interface software, is supplied for installation onto the computer 1090 and interoperation with the digital otoscope 1000. The host device driver and other software can be installed via the Internet or via portable media such as for example, a compact disc or a USB port compatible memory.

For embodiments involving the Microsoft Windows operating system, the host device driver is configured to be compliant with the Microsoft Windows Driver Model Connection Streaming Architecture (WDM-CSA). In some embodiments, the other software is supplied to provide functionality to perform still image processing, device calibration, or to conform to other manufacturing requirements etc. For example, in some embodiments, the supplied software can function to trigger otoscope image forming and capture from the host computer 1090.

Alternatively, the first communications channel 1050 can be implemented as another type of wireline communications channel, such as complying with the IEEE 1394 standard, a version of which is known as Firewire. Or, the first communications channel 1050 can be implemented as a wireless communications link, such as complying with wireless communications standards including the IEEE 802.11 or IEEE 802.15. A version of the IEEE 802.15 standard is known as the Bluetooth wireless communication standard.

The topology of the first communications link can be a point to point communications link, or as a local or wide area network communications link. Like the first communication channel 1050, the second communications channel can be implemented as a wireline or wireless type of communications link and further as point to point, or as a local or wide area network type of communications link.

In some embodiments, the computing device can be implemented as a computing device that is smaller and more portable than a personal computer, such as a personal digital assistant (PDA). Some PDA's are configured to execute Windows XP and can interoperate (transmit command and configuration information to and receive image information from) the otoscope 1000, as a Windows plug and play device.

In some embodiments, the computing device is configured to execute non Microsoft operating systems. For example, computers supplied by Apple Computer employ a NuBus architecture and also provide plug and play functionality. In this embodiment, the otoscope 1000 and its firmware are configured to interoperate with plug and play functionality of operating systems supplied by Apple Computer.

In some embodiments, image information can be transferred to a smaller device, such as an Apple IPod computing device. For example, in some use scenarios, image information is transferred from the personal computer 1090 to an IPod device (not shown) via the second communications channel.

FIG. 2 illustrates a side cross-sectional view of the embodiment of the digital otoscope 1000 of FIG. 1. The structure of the digital otoscope 1000 is mostly the same as the structure described for the non-digital otoscope (associated with a figure reference number 10) that is described within the parent patent application Ser. No. 10/897,590, herein also referred to as the '590 patent application, which is incorporated herein by reference.

Like the non-digital otoscope (10) described within the '590 patent application, the structure of the digital otoscope 1000 includes an instrument head 18, a (conical) tip element 40 having a distal end 44, a tip element retainer member 240, a distal axisymmetrical insertion portion 29 having a distal opening 29a, rotatable actuator knob 252, an inner former assembly 116, cylindrical sleeve member 144, illumination assembly 124, lamp retainer 140, and 128 miniature incandescent lamp, for example.

Further, the otoscope 1000 includes the same illumination and pneumatic system design, the same tip element attachment and removal mechanism and much of the same optical system design as described within the '590 patent application. The otoscope 1000 has much of the same focus mechanism as that of the '590 patent application. For example, the housings, focus wheel, compression spring and ball of the otoscope 1000 are the same as the non-digital otoscope (10) and provide the same detent related functionality and feel as provided by the non-digital otoscope (10).

Unlike the non-digital otoscope (10) described within the '590 patent application, the structure of the digital otoscope 1000 includes along its optical axis 27, components that are not included among the components of the '590 patent application, in order to interoperate with the image forming device 1020, which is not included within the '590 non-digital otoscope. For example, the digital otoscope 1000 includes a new lens doublet 1406 and 1408 (See FIG. 4) that is not included within the lens train of the '590 patent application.

Also, unlike the non-digital otoscope 1000 described within the '590 patent, the digital otoscope 1000 excludes the components of the '590 lens train, except for the lens doublet 96, 100. The non-digital otoscope 1000 excludes a first relay lens (104), a second relay lens (112), and lenses (190, 194) of the eyepiece mechanism, for example. Further, the digital otoscope 1000 excludes lens retainer member (176) and a ball 204, for example.

Within the non-digital otoscope (10), the focus adjustment mechanism (focus wheel) moves one or more lenses in an axial direction to adjust focus. Within the digital otoscope 1000, the focus adjustment mechanism (focus wheel) instead moves the imager, and not a lens, in an axial direction to adjust focus.

In some embodiments, the digital otoscope 1000 includes an audio input device, such as a microphone (not shown), that is configured to input audio information for storage and communication in association with the image information of the image forming device. The audio information can provide a timely explanation of the image information as it is formed, in order to enhance digital documentation of a medical inspection procedure.

In some embodiments, the otoscope 1000 includes a view finder to enable the user of the otoscope 1000 to view an image through the view finder of the otoscope at the moment of capturing an image. The view finder can be implemented as one or more eye piece lenses or as a liquid crystal display (LCD) attached to or included within the otoscope 1000.

To accommodate the view finder, the optical axis 27 can be folded, meaning that the optical axis 27 is split and a copy of the image is redirected to the view finder. In some embodiments, a single lens reflex (SLR) mirror or a beam splitter component is employed to direct the image to the image forming device and the view finder.

FIG. 3 illustrates an exploded view of a set of components residing along the optical axis 27 of the digital otoscope 1000. These components are located internal to the otoscope 1000 and are designed to enable interoperation of the imager 1202 with other components of the otoscope 1000.

As shown, the set of components includes an innerformer and cone assembly including an optics tube assembly 1310, a housing 1312, a user focus adjustment 1314, a spring 1316, an imager holder 1318, an infrared (IR) filter 1320, a face seal (dust seal for the imager) 1322, an imager 1202, an imager circuit board 1326, a USB board 1328, an imager adjuster nut 1330, a connector board 1332, an elastomeric switch 1334 and a bezel 1336.

When the otoscope 1000 is fully assembled, the user focus adjustment 1314 rotates synchronously with the focus position visual indicator 209. This mechanism enables the user of the digital otoscope 1000 to perform focus adjustment and to achieve optimal focus at a particular location that is selected by a user of the otoscope 1000.

Figure 4:
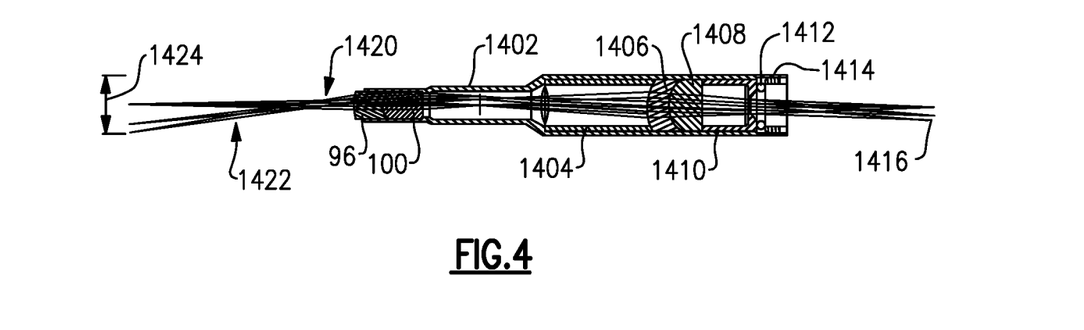
FIG. 4 illustrates a side cross-sectional view of the lens train of the digital otoscope.

FIG. 4 illustrates a side cross-sectional view of the lens train of the digital otoscope 1000. Like the non-digital otoscope (10) described within the parent '590 patent application, the lens train 1400 of the digital otoscope 1000 includes a lens doublet 96, 100 and a lens tube 1402, an o-ring 1412 and a retainer 1414 which is the same as that of the non-digital otoscope (10) described within the parent '590 patent application.

Unlike the non-digital otoscope (10) described within the parent '590 patent application, the lens train 1400 includes a new spacer 1404, a new lens doublet 1406 and 1408, a new aperture 1410, and a new imager plane 1416. The imager plane 1416 and a plane of optimal focus are located at the same location.

Unlike the non-digital otoscope (10) described within the '590 patent application, the lens train 1400 does not include a first relay lens (104) and a second relay lens (112) and lenses 190, 194 of the non-digital otoscope described within the '590 patent application. The lenses 190,194 move within the non-digital otoscope in response to focus adjustment.

Figure 5:
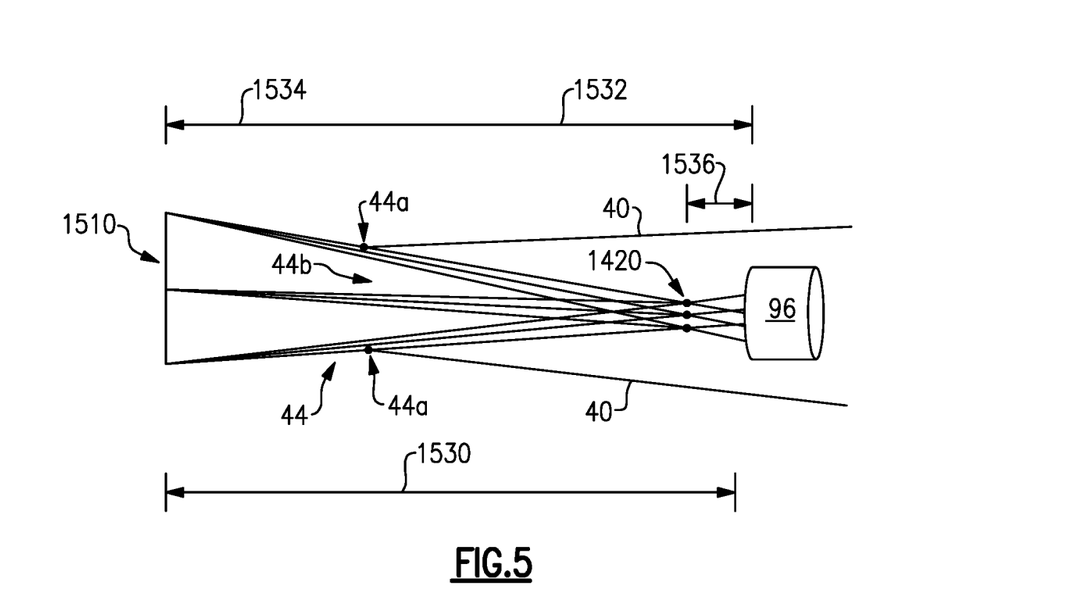
FIG. 5 is a diagram representing the field of view and the entrance pupil in relation to the most distal lens located within the tip element of the digital otoscope.

FIG. 5 illustrates a side cross-sectional view of the tip element 40 along the optical axis 27 of the otoscope 1000. As shown from this view, the distal lens 96 and a distal entrance pupil 1420 are located inside of the tip element 40. The most distal end 44 of the tip element 40 includes an opening 44b surrounded by a wall. The most distal end 44 with its opening 44b, functions as an aperture that limits light rays entering the tip element 40. The opening 44b is circular in shape (not shown from this perspective) and is substantially perpendicular to the optical axis 27. Furthermore, the opening 44b is oriented substantially parallel to and accordingly, is also referred to as facing the field of view 1510.

The opening 44b has a diameter typically equal to about 4.24 mm, also referred to as an inner diameter of the most distal end of the tip element 40. The wall of the tip that surrounds the most distal end of the tip element has a width equal to about 0.38 mm. Hence, the outer diameter of the most distal end of the tip element 40 is equal to about 5.0 mm.

The field of view 1510 is perpendicular to the optical axis 27 at a location within a volume of space that can be viewed by the imager 1202 of the otoscope 1000. In accordance with the orientation and shape of the opening 44b, the field of view 1510 has a circular shape (not shown from this perspective). The field of view increases with increasing distance away from the opening 44b.

An object within the field of view 1510 is viewable by the imager 1202 and is represented by a set of pixels within the imager 1202. The number of pixels representing an object within the field of view is referred to as the resolution of the object within the imager 1202. The resolution of an object within the field of view 1510 decreases as a function of the distance of the object from the imager 1202.

The magnification of an object is a ratio of the size of an image of the object, and the actual size of the object. Like the resolution of an object, the magnification of an object within the field of view 1510 decreases with increasing distance of the object from the imager 1202.

A working distance 1530 is defined as a distance between a location within the field of view 1510 and the distal most lens 96 of the otoscope 1000. The lens inset distance 1532, is defined as a distance between the most distal end 44a of the tip element 40 and the distal lens 96, and is equal to approximately 17.6 mm for this embodiment. The tip offset distance 1534 is equal to a distance between the most distal end 44a of the tip element 40 and a particular object within the field of view 1510, such as the tympanic membrane (not shown).

The optical characteristics of the otoscope 1000 enable forming of light received through the distal opening 44a of the tip element 40 without causing vignetting, which is the occlusion of light from different areas of the field of view. As shown, rays of light passing through the distal opening of the tip element 40 form the distal entrance pupil 1420. The rays of light exiting the distal entrance pupil 1420 expand towards the distal lens 96, but the distal lens 96 is sufficiently wide and proximate to the distal entrance pupil 1420 to intercept substantially all of the rays of light exiting the distal entrance pupil 1420.

The field of view 1510 increases in size as a function of the distance between an object within the field of view and the otoscope 1000. In this embodiment, for example, at the opening 44b of the distal end of the tip element 40, a location having a tip offset distance equaling 0.0 mm and a working distance of 17.6 mm, (pupil offset distance 14.54), the field of view 1510 has a diameter of about 4.24 mm. The size of the field of view 1510 equals the size of the opening 44b.

At a tip offset distance equal to 9.4 mm and a working distance of 27 mm, (pupil offset distance 23.94), the field of view 1510 has a diameter of about 7.0 mm. At a tip offset distance equal to 20.4 mm and a working distance of 38 mm (pupil offset equal to 34.94 mm), the field of view 1510 has a diameter of about 9.85 mm.

Figure 6A:
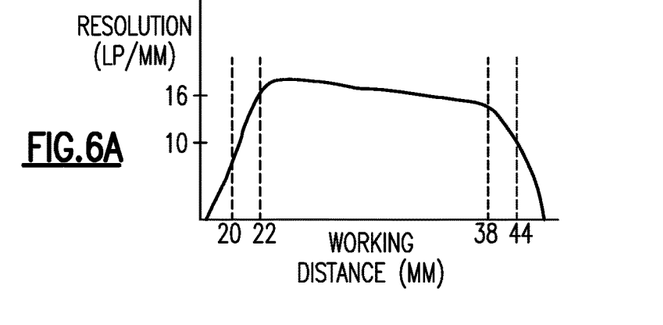
FIG. 6A is a diagram representing a distance range of optimal focus provided by the human configuration of the digital otoscope.

FIG. 6A is a diagram illustrating the optical characteristics of the human configuration of the otoscope 1000 with respect to a distance range of optimal focus. A distance range of optimal focus is a range of distance from the otoscope 1000 within which the otoscope 1000 can provide optimal focus adjustment.

By default, for the human configuration, the zoom magnification feature of the imager 1202 is off. When the imager zoom feature is off, the otoscope 1000 provides optimal focus for a field of view located within a range of working distances between 22 mm and 38 mm, which are equal to tip offset distances of 4.6 mm and 20.4 mm respectively. At optimal focus, the resolution is equal to about 16 line pairs per millimeter. When the zoom magnification mode of otoscope 1000 is on, the resolution is equal to about 28 line pairs per millimeter at optimal focus.

An object can be viewed with acceptable focus within a range of working distances between 20 and 44 mm, which are equal to tip offset distances of 2.6 mm and 26.4 mm respectively. At acceptable focus, the resolution is equal to about 10 line pairs per millimeter.

As a result, the nearest distance of an object from the distal end of the tip 40 that can be viewed or imaged with the optimal focus is 4.6 mm. The farthest distance of an object from the distal end of the tip 40 that can be viewed or imaged with the optimal focus is 20.4 mm. The above described optical characteristics yield benefits when employed within a small and confined body cavity, such as a human ear canal.

Figure 6B:
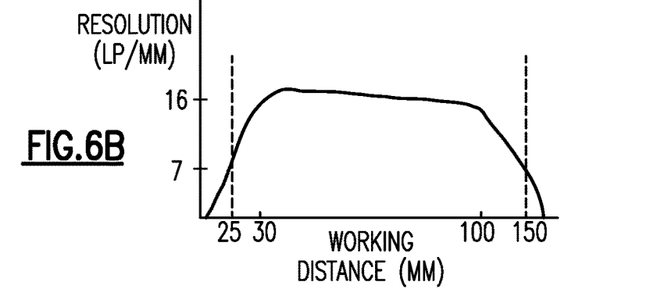
FIG. 6B is a diagram representing a distance range of optimal focus provided by the veterinary configuration of the digital otoscope.

FIG. 6B is a diagram illustrating the optical characteristics of the veterinary configuration of the otoscope 1000 with respect to a distance range of optimal focus. By default, for the veterinary configuration, the zoom feature of the imager 1202 is on. In some veterinary embodiments, the zoom feature cannot be turned off.

When the imager zoom feature is on, the otoscope 1000 provides optimal focus for a field of view located within a range of working distances between 30 mm and 100 mm, equal to tip offset distances of 12.4 mm and 82.4 mm respectively. The expanded distance range of optimal focus accommodates much larger ear canals possessed by some animals, such as dogs and cats for example.

As a result, the nearest distance of an object from the distal end of the tip 40 that can be viewed or imaged with the optimal focus is 12.4 mm. The farthest distance of an object from the distal end of the tip 40 that can be viewed or imaged with the optimal focus is 82.4 mm. These optical characteristics are useful when employed within a small and confined cavity, such as a an ear canal of a veterinary subject.

Figure 7A:
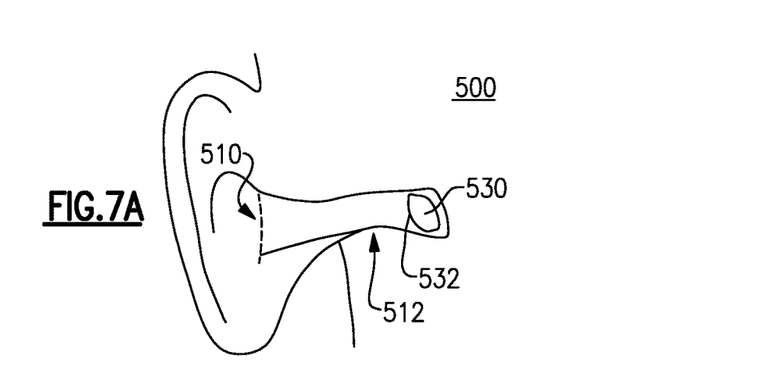
FIG. 7A is an illustration of a typical human ear canal.

FIG. 7A is an illustration of a typical human ear canal 500. As shown, the ear canal includes an opening 510 and a tympanic membrane (ear drum) 530 located within it. A perspective of the tympanic membrane (ear drum) 530 as seen from the opening 510 of the ear canal 500, has a large profile, referred to herein as its visible profile. The visible profile of the ear drum 530 shows substantially one side of the ear drum, referred to as the visible side of the ear drum. The visible side of the ear drum 530 is somewhat circular in overall shape and has an average diameter width of about 7 mm. Also, the visible side has a center point 532 along a surface that faces somewhat downward and away relative to the opening of the ear canal, and is referred to as being tilted.

A distance between the opening 510 of the ear canal and the center point 532 of the visible profile of the tympanic membrane is 20 mm. Each cross-section of the ear canal 500, that faces and is visible from the perspective of the opening 510, is also some what circular. Because each cross-section of the ear canal it is not exactly circular, each cross-section does not have a uniform (constant) width (diameter) as a circular cross-section would have. To address this circumstance, the width of each cross-section of the ear canal will be defined as the distance from its upper most surface to its lower most surface, which is discernable from the perspective of this figure.

Accordingly, as illustrated, the width of the cross-section of ear canal at its opening is approximately 8 mm. Moving from the opening 510 towards the ear drum 530, the cross-section of the ear canal narrows. At a location 512 of about 16 mm from the opening 510, the cross-section of the ear canal narrows to approximately 5 mm. Moving further towards the ear drum 530, the cross-section of the ear canal widens to in excess of 5 mm at the ear drum 530.

Actual dimensions of each human ear canal vary across the entire human population and a compilation of which forms a statistical distribution. It is understood that the typical ear canal 500 is located at or substantially proximate to the center, also referred to as the mean or median, of the aforementioned statistical distribution.

Figure 7B:
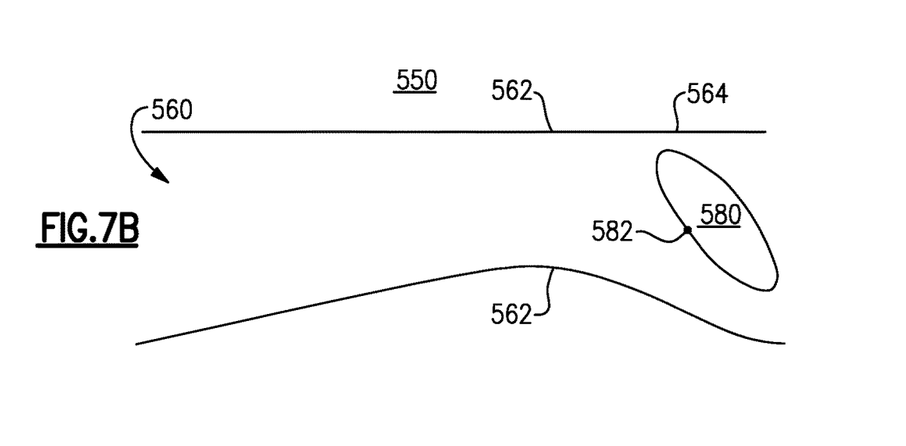
FIG. 7B illustrates a representative human ear canal.

FIG. 7B illustrates a representative human 550 ear canal that represents and approximates the typical human ear canal of FIG. 5A. The representative ear canal 550 is a useful model that illustrates the operation of the otoscope 1000 within an environment that it is designed to work within.

The representative ear canal 550 has an upper surface that is horizontal (level) and a lower surface is not parallel to its upper surface and that rises gradually towards the ear drum 580, and has a cross-section between its opening 560 and its ear drum 580 is circular in shape. The diameter width of the cross-section of the representative ear canal 550 varies linearly between its opening 560 and the ear drum 580. At a location of its opening 560, the diameter of the representative ear canal 550, also referred to as its width or diameter width, is equal to 8 mm. At a location 562 that is located 16 mm inside of the opening of the representative ear canal 550, the diameter width of its cross-section is equal to 5 mm.

The diameter width of the cross-section of the representative ear canal 550 varies and narrows linearly between location 560 and location 562. The diameter width of the cross-section of the representative ear canal 550 widens linearly between location 562 and location 564 which is located at about the center point 582 of the visible profile of the ear drum. The location 564 is located 20 mm inside of the opening 560 of the representative ear canal 550.

Figure 8:
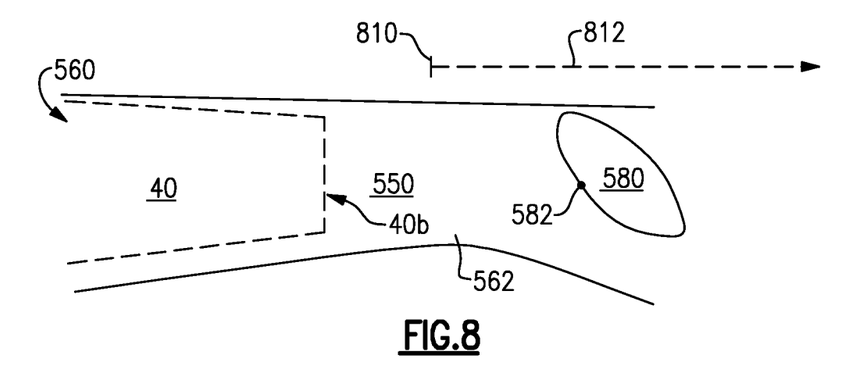
FIG. 8 illustrates placement of the tip element within the representative human ear canal.

FIG. 8 illustrates placement of the tip element 40 within the representative human ear canal 550. As shown, the tip element 40 is placed about midway into the ear canal 550. The distal end of the tip element 40 is located 10 mm inside of the ear canal 550 from its opening 560.

At this location, the ear drum 580 is well within the distance range of optimal focus provided by the otoscope 1000 in its human configuration (See FIG. 6A). The range of optimal focus starts a location 810 that is 4.4 mm from the distal opening 44b (4.6 mm before the ear drum) and ends 20.4 mm from the distal opening 44b, extending 812 well beyond the most distant portion of the ear drum 580 and tissue surrounding the ear drum 580.

In this location, the field of view at the location of the center point of the visible profile of the ear drum 580 has a diameter of 7 mm, which is more that sufficient to encompass the entire eardrum 580 within the formed still or live image. Using focus position visual indicator 209, still or live image information is obtained via the otoscope 1000 with optimal focus and maximum visual acuity.

There may be circumstances where it is difficult to insert the tip element 40 into the ear canal 550. For example, an ear canal may be infected and/or be cluttered with cerumen (ear wax). In these circumstances, the distance range of optimal focus continues to enable image information to be formed with optimal.

For example, if distal opening 44b of the tip element 40 can only be inserted 5 mm into the ear canal 550, the ear drum 580 is located 15 mm from the distal opening 44b and remains well within the distance range of optimal focus. The field of view 1510 at this location exceeds a diameter of 7 mm. Using focus position visual indicator 209, still or live image information of the entire eardrum 580 and its anatomical details (surrounding tissue) is formed via the otoscope 1000 with optimal.

Even if the distal opening 44b of the tip element 40 cannot be inserted into the ear canal 550 and is constrained to be located at the opening 560 of the ear canal 550, the ear drum 580 within the distance range of optimal focus. In this circumstance, the ear drum is located 20 mm from the distal opening 44b while the range of optimal focus extends to a distance of 20.4 mm from the distal opening. Beyond 20.4 mm, the focus is near optimal and acceptable within an additional 6 mm (See FIG. 6A).

Optionally, in this circumstance, the zoom magnification mode can be set on. As a result, the ear drum and surrounding tissue are entirely within the range of optimal focus (See FIG. 6B) and the magnification is doubled to reveal finer detail to the imager and the user.

Figure 9:
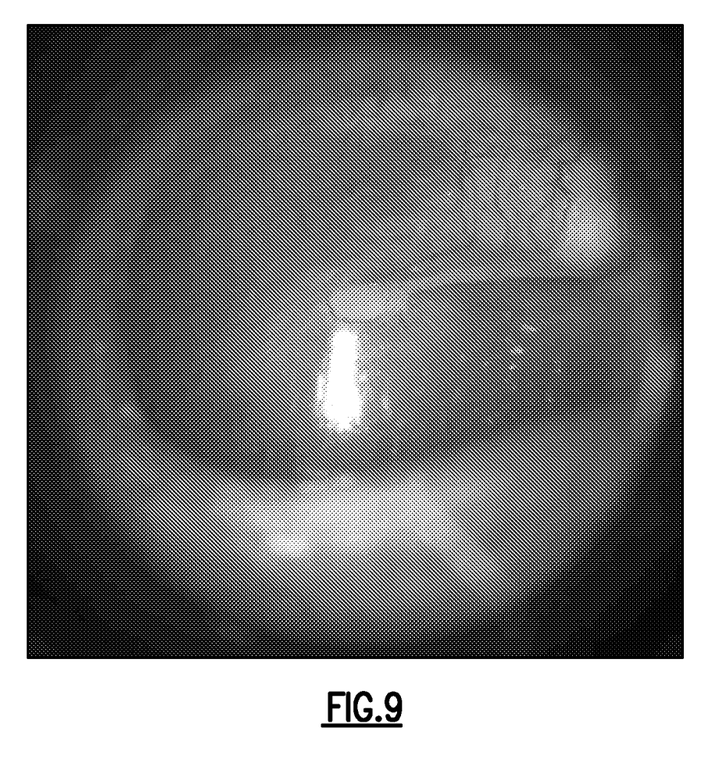
FIG. 9 illustrates an image of a tympanic membrane formed from the digital otoscope 1000 at or near optimal focus.

FIG. 9 illustrates an image of a tympanic membrane formed from the digital otoscope 1000 at or near optimal focus. As shown, small details of the entire tympanic membrane including fine blood vessels are visible from the otoscope 1000. These small details are visible at a location in excess of 10 mm from the distal opening 44a of the tip element 40.

The following summarizes some of aspects of the invention. In some embodiments, the invention provides for an otoscope including an instrument head having a distal insertion portion for insertion into an ear, the distal insertion portion having a distal opening, an axisymmetric tip element releasably attached to the distal insertion portion, the tip element having a distal opening; and an optical system contained within the instrument head, the optical system including a plurality of optical components and an aperture stop about which the optical components are disposed, the optical system forming an entrance pupil distal to the distal opening of the distal insertion portion but proximal to the distal opening of the attached tip element, the optical system further including an image forming device that is configured to form image information that represents a still or a live image of a target of interest aligned along an optical axis with the distal opening, the optical system being capable of capturing substantially the entire tympanic membrane of a patient at one instant in time.

In some embodiments, the invention provides an otoscope including an instrument head having a distal insertion portion for insertion into an ear of a human or veterinary subject, the distal insertion portion having a distal opening, an tip element releasably attached to the distal insertion portion, the tip element having a distal opening; and an optical system contained within the instrument head, the optical system including a plurality of optical components; and where the optical system further includes a viewing component for viewing of an image of a target of interest aligned along an optical axis disposed within the distal opening, and the optical system being configured to provide a field of having a diameter equaling at least 7 mm at a distance of at least 15 mm from a distal opening of the attached tip element; and the optical system being further configured to simultaneously provide a distance range of optimal focus having a range of at least 8 mm, the distance range of optimal focus including a location at a working distance equal to about 30 mm.

Optionally, the otoscope is configured so that the distal opening of the attached tip element can be inserted into a representative human ear to within at least 10 mm of a tympanic membrane. Optionally, the optical system being further configured to simultaneously provide a range of magnification of an object within the field of view within a range of between about 0.4 and about 0.6.

In some embodiments, the optical system includes an entrance pupil having a diameter that is less than 5 mm and that is located outside of the instrument head and within the attached tip element. Optionally, the viewing component is an eyepiece including at least one optical element. Optionally, the otoscope includes a focusing mechanism that is user accessible and that moves a lens along the optical axis. Optionally, the viewing component is an image forming device that is configured to form image information and where the device has a zoom magnification feature.

In some embodiments, the otoscope includes a focusing mechanism that is user accessible and that moves the image forming device along the optical axis. Optionally, the otoscope provides a field of view equal to at least 7 mm at a working distance of less than or equal to 35 mm.

In other embodiments, the otoscope includes a digital image forming device having a zoom magnification feature, an instrument head having a distal insertion portion for insertion into an ear of a human or veterinary subject, the distal insertion portion having a distal opening, an tip element having a distal opening; and an optical system contained within the instrument head, the optical system including a plurality of optical components; and where the optical system having a tip element configured to penetrate at least 5 mm into a representative ear canal and providing an distance range of optimal focus having a length of at least 5 mm.

In other embodiments, the invention provides an otoscope including an instrument head having a distal insertion portion for insertion into an ear of a human or veterinary subject, the distal insertion portion having a distal opening, a tip element having a distal opening; and an optical system contained within the instrument head, the optical system including a plurality of optical components; and where the tip element configured to receive penetrate a representative ear canal by at least 5 mm and receiving a field of view having a diameter of at least 7 mm at a working distance equal to less than or equal to 50 mm from the distal opening.

Optionally, the field of view is received at a working distance of less than or equal to 40 mm. Optionally, the field of view is received at a working distance of less than or equal to 30 mm.

In some embodiments, a distance range of optimal focus has a length of greater than or equal to 5 mm. Optionally, a distance range of optimal focus has a length of greater than or equal to 10 mm and includes location at a working distance equal to 32 mm.

In some embodiments, the otoscope has a zoom feature. Optionally, the zoom feature enables a distance range of optimal focus having a length of at least 35 mm. Optionally, the distance range of optimal focus includes a location of a working distance equal to 65 mm.

In some embodiments, the otoscope is configurable where the field of view is received at a working distance of less than or equal to 60 mm.

While the present invention has been explained with reference to the structure disclosed herein, it is not confined to the details set forth and this invention is intended to cover any modifications and changes as may come within the scope and spirit of the following claims.

What is claimed is:

1. An otoscopic instrument comprising:
    an instrument head including a distal end and a proximal end;
    a handle supporting the instrument head, the handle retaining at least one battery;
    an imager disposed within the instrument head and configured to capture at least one of single images or video of a medical target;
    a display coupled to the at least one battery and imager;
    a user interface; and
    a processor coupled to the imager and display, the display disposed at the proximal end of the instrument head and configured to present an image of a medical target captured by the imager and in which the user interface is also disposed at the proximal end of the instrument head and configured to enable at least two operating modes.

2. The instrument according to claim 1, wherein the user interface comprises at least one control button.

3. The instrument according to claim 1, further comprising a light source for illuminating the medical target.

4. The instrument according to claim 3, further comprising a set of optical fibers extending between the light source and the distal end of the instrument head.

5. The instrument according to claim 1, in which the distal end of the instrument head is configured to releasably support a tip element.

6. The instrument according to claim 5, in which the tip element is shaped to prevent entry into the ear canal of a patient beyond a predetermined distance.

7. The instrument according to claim 1, further comprising at least one optic disposed within the instrument head and aligned with the imager along an imaging axis.

8. The instrument according to claim 1, wherein the operating modes include a first viewing mode and a second viewing mode.

9. The instrument according to claim 1, further comprising means for focusing the imager relative to a medical target.

10. The instrument according to claim 1, further comprising memory for storing images or video captured by the imager.

11. The instrument according to claim 10, further comprising a USB port.

12. The instrument according to claim 1, wherein the display is an LCD.

13. A method for assembling an otoscopic instrument, said method comprising:
    providing an instrument head including a distal end and a proximal end;
    attaching a handle for supporting the instrument head, the handle retaining at least one battery;
    providing an imager within the instrument head;
    providing a processor within the instrument head;
    providing a user interface at the proximal end of the instrument head, wherein the user interface is coupled to the processor and selectively enables multiple viewing modes; and
    coupling a display coupled to the at least one battery, processor and imager and disposing the display at the proximal end of the instrument head, wherein the display is configured to present an image of a medical target captured by the imager.

14. The method according to claim 13, wherein the user interface comprises at least one control button.

15. The method according to claim 13, wherein the imager is configured to capture images or video of a medical target.

16. The method according to claim 15, further comprising:
    providing memory for storing images or video captured by the imager.

17. The method according to claim 16, further comprising:
    providing a USB port to enable stored video or images captured by the imager to be downloaded.

* * * * *